(12) United States Patent
Kraus et al.

(10) Patent No.: US 6,629,613 B1
(45) Date of Patent: Oct. 7, 2003

(54) LEUKOCYTE FILTER

(75) Inventors: Menachem Kraus, Rehovot (IL); Yefet Gamlieli, Kiryat Ekron (IL)

(73) Assignee: Teva Medical Ltd., Ashdod (IL)

( * ) Notice: Subject to any disclaimer, the term of this patent is extended or adjusted under 35 U.S.C. 154(b) by 0 days.

(21) Appl. No.: 09/693,427

(22) Filed: Oct. 23, 2000

(30) Foreign Application Priority Data

Jun. 28, 2000 (IL) .................................................. 137077

(51) Int. Cl.$^7$ ......................... B01D 29/00; B01D 29/50; B01D 39/00
(52) U.S. Cl. ........................ 210/489; 210/483; 210/488
(58) Field of Search ................................. 210/483, 488, 210/489, 496, 503, 505

(56) References Cited

U.S. PATENT DOCUMENTS

| | | | |
|---|---|---|---|
| 4,985,153 A | 1/1991 | Kuroda et al. | 210/782 |
| 5,164,087 A | 11/1992 | Naoi et al. | 210/500.1 |
| 5,234,593 A | 8/1993 | Kuroki et al. | 210/496 |
| 5,476,587 A | 12/1995 | Kuroki et al. | 210/496 |
| 5,478,470 A | 12/1995 | Fukuda et al. | 210/500.1 |
| 5,665,233 A | 9/1997 | Fukuda et al. | 210/483 |
| 5,707,520 A | 1/1998 | Kuroki et al. | 210/436 |
| 5,707,526 A | 1/1998 | Kraus et al. | 210/650 |
| 5,783,094 A | 7/1998 | Kraus et al. | 210/767 |
| 5,820,755 A | 10/1998 | Kraus et al. | 210/483 |
| 5,895,575 A | 4/1999 | Kraus et al. | 210/483 |

FOREIGN PATENT DOCUMENTS

| | | |
|---|---|---|
| EP | 408462 B1 | 1/1991 |
| JP | 55-136955 | 10/1980 |
| JP | 50-34337 | 2/1993 |
| JP | 51-48150 | 6/1993 |
| JP | 52-62656 | 10/1993 |

OTHER PUBLICATIONS

VERSAPOR® Membrane Catalogue, manufactured by Pall–Gelman Corp., New York, 1995.
NYLON MAGNA® Membrane Catalogue, MSI–Osmonics, Massachusetts, 1999.

Primary Examiner—John Kim
(74) Attorney, Agent, or Firm—Ladas & Parry (57) ABSTRACT

There is provided a leukocyte filter comprising: a prefilter portion; and a membrane filter portion downstream of the prefilter portion, the membrane filter portion having a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In a preferred embodiment, no more than 60% of the pore volume is constituted by pores having a pore cross section diameter larger than 10 microns. In another preferred embodiment, the membrane filter portion is characterized in that no more than 30% of the pore volume is constituted by pores having a pore cross section diameter less than 3 microns. In a preferred embodiment, the membrane filter portion is characterized in that no more than 30% of the pore volume is constituted by pores having a pore cross section diameter less than 3 microns. There is also provided a filtering method and a filtered blood product, including a filtered whole blood product.

4 Claims, 5 Drawing Sheets

LEUKOCYTE FILTER

FIELD OF THE INVENTION

The present invention relates to leukocyte filters and filtration generally.

BACKGROUND OF THE INVENTION

Filters are commonly used to remove leukocytes from blood and blood products in order to minimize various adverse effects of white cell transfusion. Examples of adverse effects include non-hemolytic febrile reaction, alloimmunization and graft versus host disease. Commercial leukoreduction filters are mostly composed of non-woven materials, which are made up of discrete fibers bonded or pressed together.

Another filter known in the art is a membrane filter, which, instead of having discrete fibers, is a continuous structure containing a network of pores. The membrane enables efficient capture of leukocytes and a reasonably good passage of the desired blood components (e.g., erythrocytes, platelets or plasma). However, membrane filters known in the art are either lacking in performance or require specific materials of construction, unusual pore morphology, a very narrow pore size distribution or pore size gradation within the filter.

One example of a membrane filter is described in U.S. Pat. No. 5,895,575 assigned to the present applicant/assignee, the disclosure of which is incorporated herein by reference. The '575 patent describes a filter composed of nitrocellulose membranes and non-woven materials.

U.S. Pat. No. 5,476,587 (Kuroki et al.) describes a membrane with a most frequent pore diameter of 1–5 $\mu$m, and a pore size weight average to number average ratio of 1.5 to 2.5, the ratio gradually changing from the top to the bottom of the filter.

U.S. Pat. No. 5,707,526 (a continuation-in-part of Kuroki et al.'s '587 patent) describes a membrane having a most frequent pore diameter of 1–5 $\mu$m, and a specific dust permeability, enclosed in a housing of a specially designed structure.

U.S. Pat. No. 5,478,470 (Fukuda et al.) describes membranes with a specific set of properties, including pores of 2–30 $\mu$m having a combined pore volume equal to or greater than 94% of the total pore volume.

U.S. Pat. No. 5,665,233 (a division of Fukuda et al.'s '470 patent) describes the use of porous materials, including membranes, having a specific set of properties, among them certain pore volumes, pore size gradation, leukocyte retention per layer, and layer thickness of less than 0.5 mm.

European Patent Application Publication No. 0406,485 A1 (now abandoned) describes membrane containing filters, wherein the membranes are strongly asymmetric, having a median pore size at the upstream surface substantially larger than at the downstream surface.

Japanese Patent Application No. 526,2656 describes membranes with a negative charge. Japanese Patent Application No. 503,4337 describes membranes made specifically of polyvinyl format or polyurethane. Japanese Patent Application No. 514,8150 describes a filter containing both porous materials and a non-woven fabric with fibers of 0.8–3 $\mu$m diameter. Japanese Patent Application No. 54-44270 (filed Apr. 13, 1979) describes a polyester foam used to trap leukocytes.

Other membrane filters are described in European Patent Publication No. 408,462 B1 and U.S. Pat. No. 5,234,593, both of which have unusual pore structures, and in U.S. Pat. Nos. 4,985,153 and 5,783,094. The disclosures of all publications mentioned in the present specification are incorporated herein by reference.

In general in the prior art, membrane filters are constructed of specialized or non-commercial materials with narrow ranges of pore sizes. In addition, the filters generally have a non-homogeneous pore structure throughout their bulk, i.e. they employ membranes wherein the pores of the membranes have large diameter on one side of the membrane and a narrower diameter on the other side. Also, it has been assumed in the prior art that in order to obtain good throughput and prevent filter clogging, the filter must have a multilayer structure with a gradual decrease in pore size in the direction of flow.

SUMMARY OF THE INVENTION

The present invention seeks to provide an improved leukocyte filter, a filtering method and a filtered blood product, including a filtered whole blood product.

There is thus provided in accordance with a preferred embodiment of the present invention a leukocyte filter comprising: a prefilter portion; and a membrane filter portion downstream of the prefilter portion, the membrane filter portion having a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

In accordance with a preferred embodiment of the invention, no more than 60% of the pore volume is constituted by pores having a pore cross section diameter larger than 10 microns. In accordance with a preferred embodiment of the invention, the membrane filter portion is characterized in that no more than 30% of the pore volume is constituted by pores having a pore cross section diameter less than 3 microns. In accordance with a preferred embodiment of the invention, the membrane filter portion is characterized in that no more than 30% of the pore volume is constituted by pores having a pore cross section diameter less than 3 microns.

There is also provided, in accordance with a preferred embodiment of the invention, a leukocyte filter comprising: a prefilter portion; and a membrane filter portion downstream of the prefilter portion, the prefilter portion being characterized in that it captures less than 60% of incoming leukocytes, and the membrane filter portion being characterized in that it is non-cellulosic and generally homogeneous. In accordance with a preferred embodiment of the invention, the membrane filter portion is characterized in that it has a pore surface area/membrane volume ratio larger than 6 square meters per milliliter of membrane volume. In accordance with a preferred embodiment of the invention, the membrane filter portion is characterized in that it has a pore surface area/membrane mass ratio larger than 12 square meters per gram of membrane. In accordance with a preferred embodiment of the invention, the membrane filter portion comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter portion is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter portion is characterized in that at least 40% of its pore volume is constituted by pores having a pore cross section diameter of between 3 and 10 microns. In accordance with a preferred embodiment of the invention, the membrane filter portion is characterized in that at least 5% of the pore volume is constituted by pores having a pore cross section diameter larger than 10 microns. In accordance with a preferred embodiment of the invention, the membrane filter portion is characterized in that no more than 30% of the pore volume being constituted by pores having a pore cross section diameter less than 3 microns. In accordance with a preferred embodiment of the invention, the membrane filter portion is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided, in accordance with a preferred embodiment of the invention, a leukocyte filter comprising: a prefilter portion; and a membrane filter portion downstream of the prefilter portion, said membrane filter portion being characterized in that it has a pore surface area/ membrane volume ratio larger than 6 square meters per milliliter of membrane volume. In accordance with a preferred embodiment of the invention, the membrane filter portion is characterized in that the cumulative surface area of pores having a pore diameter of 2–30 microns is less than 30% of the total surface area of the membrane. In accordance with a preferred embodiment of the invention, the membrane filter portion is characterized in that it has a pore surface area/membrane mass ratio larger than 12 square meters per gram of membrane. In accordance with a preferred embodiment of the invention, the membrane filter portion comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter portion comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter portion is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter portion is characterized in that at least 40% of its pore volume is constituted by pores having a pore cross section diameter of between 3 and 10 microns. In accordance with a preferred embodiment of the invention, the membrane filter portion is characterized in that at least 5% of the pore volume is constituted by pores having a pore cross section diameter larger than 10 microns. In accordance with a preferred embodiment of the invention, the membrane filter portion is characterized in that no more than 30% of the pore volume being constituted by pores having a pore cross section diameter less than 3 microns. In accordance with a preferred embodiment of the invention, the membrane filter portion is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filter comprising: a prefilter portion; and a membrane filter portion downstream of the prefilter portion, said membrane filter portion being characterized in that it has a pore surface area/ membrane mass ratio larger than 12 square meters per gram of membrane.

There is also provided in accordance with a preferred embodiment of the invention, the a leukocyte filter comprising: a prefilter portion; and a membrane filter portion downstream of the prefilter portion, said membrane filter portion comprising at least one layer of a generally homogeneous non-cellulsoic membrane, wherein the total pore volume of pores having a diameter between 1–30 microns is less than 90% of the total pore volume. In accordance with a preferred embodiment of the invention, the membrane filter portion is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter portion is characterized in that at least 40% of its pore volume is constituted by pores having a pore cross section diameter of between 3 and 10 microns. In accordance with a preferred embodiment of the invention, the membrane filter portion is characterized in that at least 5% of the pore volume is constituted by pores having a pore cross section diameter larger than 10 microns. In accordance with a preferred embodiment of the invention, the membrane filter portion is characterized in that no more than 30% of the pore volume is constituted by pores having a pore cross section diameter less than 3 microns. In accordance with a preferred embodiment of the invention, the membrane filter portion is characterized in that at least 40% of its pore volume is constituted by pores having a pore cross section diameter of between 3 and 10 microns. In accordance with a preferred embodiment of the invention, the membrane filter portion is characterized in that at least 5% of the pore volume is constituted by pores having a pore cross section diameter larger than 10 microns. In accordance with a preferred embodiment of the invention, the membrane filter portion is characterized in that no more than 30% of the pore volume is constituted by pores having a pore cross section diameter less than 3 microns.

There is also provided in accordance with a preferred embodiment of the invention, a leukocyte filter comprising: a prefilter portion; and a membrane filter portion downstream of the prefilter portion, said membrane filter portion having at least 40% of its pore volume being constituted by pores having a pore cross section diameter of between 3 and 10 microns. In accordance with a preferred embodiment of the invention, the membrane filter portion is characterized in that at least 5% of the pore volume is constituted by pores having a pore cross section diameter larger than 10 microns. In accordance with a preferred embodiment of the invention, the membrane filter portion is characterized in that no more than 30% of the pore volume is constituted by pores having a pore cross section diameter less than 3 microns. In accordance with a preferred embodiment of the invention, the membrane filter portion is characterized in that no more than 30% of the pore volume is constituted by pores having a pore cross section diameter less than 3 microns.

There is also provided in accordance with a preferred embodiment of the invention a leukocyte filter comprising: a prefilter portion; and a membrane filter portion downstream of the prefilter portion, said membrane filter portion having at least 5% of the pore volume being constituted by pores having a pore cross section diameter larger than 10 microns.

There is also provided in accordance with a preferred embodiment of the invention a leukocyte filter comprising: a prefilter portion; and a membrane filter portion downstream of the prefilter portion, said membrane filter portion having no more than 30% of the pore volume being constituted by pores having a pore cross section diameter less than 3 microns.

There is also provided in accordance with a preferred embodiment of the invention a leukocyte filtering method comprising: supplying a blood product to be filtered of leukocytes to a prefilter which captures less than 60% of incoming leukocytes; and supplying prefiltered blood products to a non-cellulosic and generally homogeneous membrane filter; wherein said blood product to be filtered of leukocytes has had the content of at least one blood component removed or reduced, relative to the content of said at least one component in whole blood, prior to the step of supplying the blood product to be filtered of leukocytes to the prefilter. In accordance with a preferred embodiment of the invention, the membrane filter is characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio layer than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filtering method comprising: supplying a blood product to be filtered of leukocytes to a prefilter; and supplying prefiltered blood product to a membrane filter downstream of the prefilter, said membrane filter being characterized in that it has a pore surface area/membrane volume ratio larger than 6 square meters per milliliter of membrane volume; wherein said blood product to be filtered of leukocytes has had the content of at least one blood component removed or reduced, relative to the content of said at least one component in whole blood, prior to the step of supplying the blood product to be filtered of leukocytes to the prefilter. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter comprises at least one layer of a non-cellulosic membrane, wherein the total pore volume of pores having a diameter between 1–30 microns is less than 90% of the total pore volume. In accordance with a preferred embodiment of the invention, the non-cellulosic membrane is a generally homogeneous membrane. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filtering method comprising: supplying a blood product to be filtered of leukocytes to a prefilter; and supplying prefiltered blood product to a membrane filter downstream of the prefilter, said membrane filter being characterized in that it has a pore surface area/membrane mass ratio larger than 12 square meters per gram of membrane; wherein said blood product to be filtered of leukocytes has had the content of at least one blood component removed or reduced, relative to the content of said at least one component in whole blood, prior to the step of supplying the blood product to be filtered of leukocytes to the prefilter.

There is provided in accordance with a preferred embodiment of the invention a leukocyte filtering method comprising: supplying a blood product to be filtered of leukocytes to a prefilter; and supplying prefiltered blood product to a membrane filter comprising at least one layer of a non-cellulosic membrane, wherein the total pore volume of pores having a diameter between 1–30 microns is less than 90% of the total pore volume; wherein said blood product to be filtered of leukocytes has had the content of at least one blood component removed or reduced, relative to the coment of said at least one component in whole blood, prior to the step of supplying the blood product to be filtered of leukocytes to the prefilter. In accordance with a preferred embodiment of the invention, the non-cellulosic membrane is a generally homogeneous membrane. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention a leukocyte filtering method comprising: supplying a blood product to be filtered of leukocytes to a prefilter; and supplying prefiltered blood product to a membrane filter downstream of the prefilter, said membrane filter being characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns; wherein said blood product to be filtered of leukocytes has had the content of at least one blood component removed or reduced, relative to the content of said at least one component in whole blood, prior to the step of supplying the blood product to be filtered of leukocytes to the prefilter. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention a leukocyte filtering method comprising: supplying a blood product to be filtered of leukocytes to a prefilter; and supplying prefiltered blood product to a membrane filter downstream of the prefilter, said membrane filter being characterized in that at least 40% of its pore volume is constituted by pores having a pore cross section diameter of between 3 and 10 microns; wherein said blood product to be filtered of leukocytes has had the content of at least one blood component removed or reduced, relative to the content of said at least one component in whole blood, prior to the step of supplying the blood product to be filtered of leukocytes to the prefilter. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filtering method comprising: supplying a blood product to be filtered of leukocytes to a prefilter; and supplying prefiltered blood product to a membrane filter having at least 5% of its pore volume constituted by pores having a pore cross section diameter larger than 10 microns; wherein said blood product to be filtered of leukocytes has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtering method comprising: supplying a blood product to be filtered of leukocytes to a prefilter; and supplying prefiltered blood product to a membrane filter downstream of the prefilter, said membrane filter being characterized in that no more than 30% of its pore volume is constituted by pores having a pore cross section diameter less than 3 microns; wherein said blood product to be filtered of leukocytes has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method including: supplying a blood product to be filtered of leukocytes to a prefilter which captures less than 60% of incoming leukocytes; and supplying prefiltered blood product to a non-cellulosic and generally homogeneous membrane filter; wherein the leukocyte filtered blood product has had the content of at least one blood component removed or reduced, relative to the content of said at least one component in whole blood, prior to the step of supplying the blood product to be filtered of leukocytes to the prefilter. In accordance with a preferred embodiment of the invention, the membrane filter is characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention a leukocyte filtered blood product produced by a method comprising: supplying a blood product to be filtered of leukocytes to a prefilter; and supplying prefiltered blood product to a membrane filter downstream of the prefilter, said membrane filter being characterized in that it has a pore surface area/membrane volume ratio larger than 6 square meters per milliliter of membrane volume; wherein the leukocyte filtered blood product has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method comprising: supplying a blood product to be filtered of leukocytes to a prefilter; and supplying prefiltered blood product to a membrane filter downstream of the prefilter, said membrane filter being characterized in that it has a pore surface area/membrane mass ratio larger than 12 square meters per gram of membrane; wherein the leukocyte filtered blood product has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method comprising: supplying a blood product to be filtered of leukocytes to a prefilter; and supplying prefiltered blood product to a membrane filter downstream of the prefilter, said membrane filter being characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns; wherein the leukocyte filtered blood product has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method comprising: supplying a blood product to be filtered of leukocytes to a prefilter, and supplying prefiltered blood product to a membrane filter downstream of the prefilter, said membrane filter being characterized in that at least 40% of its pore volume is constituted by pores having a pore cross section diameter of between 3 and 10 microns; wherein said leukocyte filtered blood product has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method comprising: supplying a blood product to be filtered of leukocytes to a prefilter; and supplying prefiltered blood product to a membrane filter having at least 5% of its pore volume constituted by pores having a pore cross section diameter larger than 10 microns; wherein said leukocyte filtered blood product has had the content of at least one blood component removed or reduced, relative to the content of said at least one component in whole blood, prior to the step of supplying the blood product to be filtered of leukocytes to the prefilter.

There is also provided in accordance with a preferred embodiment of the invention a leukocyte filtered blood product produced by a method comprising: supplying a blood product to be filtered of leukocytes to a prefilter; and supplying prefiltered blood product to a membrane filter downstream of the prefilter, said membrane filter being characterized in that no more than 30% of its pore volume is constituted by pores having a pore cross section diameter less than 3 microns; wherein said leukocyte filtered blood product has had the content of at least one blood component removed or reduced, relative to the content of said at least one component in whole blood, prior to the step of supplying the blood product to be filtered of leukocytes to the prefilter.

There is also provided, in accordance with a preferred embodiment of the invention, a leukocyte filtering method, comprising: supplying whole blood to a prefilter; and supplying prefiltered blood to a membrane filter downstream of the prefilter, said membrane filter being characterized in that it comprises at least two non-cellulosic membranes having generally the same degree of symmetry and each having a thickness of less than about 0.25 mm; characterized in that the prefilter and membrane filter, operating together, reduce the number of leukocytes present in one unit of whole blood to no more than five million. In accordance with a preferred embodiment of the invention, the prefilter and membrane filter, operating together, reduce the number of leukocytes present in one unit of whole blood to no more than one million. In accordance with a preferred embodiment of the invention, the filtered blood product also contains at least 60% of the platelets contained in the whole blood before filtration and at least 85% of the red cells contained in the whole blood before filtration.

There is also provided in accordance with a preferred embodiment of the invention a leukocyte filtering method comprising: whole blood to a prefilter which captures less than 60% of incoming leukocytes; and supplying prefiltered whole blood to a non-cellulosic and generally homogeneous membrane filter. In accordance with a preferred embodiment of the invention, the membrane filter is characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger that 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 50% of the pore volume being constituted by pores having a pore cross section diameter larger than 10 microns.

There is also provided in accordance with a preferred embodiment of the invention a leukocyte filtering method comprising: supplying whole blood to a prefilter; and supplying prefiltered whole blood to a membrane filter downstream of the prefilter, said membrane filter being characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter comprises at least one layer of a non-cellulosic membrane, wherein the total pore volume of pores having a diameter between 1–30 microns is less than 90% of the total pore volume. In accordance with a preferred embodiment of the invention, the non-cellulosic membrane is a generally homogeneous membrane. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filtering method comprising: supplying whole blood to a prefilter; and supplying prefiltered whole blood to a membrane filter downstream of the prefilter, and membrane filter being characterized in that it has a pore surface area/membrane mass ratio larger than 12 square meters per gram of membrane.

There is also provided in accordance with a preferred embodiment of the invention a leukocyte filtering method comprising: supplying whole blood to a prefilter; and supplying prefiltered whole blood to a membrane filter comprising at least one layer of a non-cellulosic membrane, wherein the total pore volume of pores having a diameter between 1–30 microns is less than 90% of the total pore volume. In accordance with a preferred embodiment of the invention, the non-cellulosic membrane is a generally homogeneous membrane. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention a leukocyte filtering method comprising: supplying whole blood to a prefilter; and supplying prefiltered whole blood to a membrane filter downstream of the prefilter, said membrane filter being characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention a leukocyte filtering method comprising: supplying whole blood to a prefilter; and supplying prefiltered whole blood to a membrane filter downstream of the prefilter, said membrane filter being characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention a leukocyte filtering method comprising: supplying whole blood to a prefilter; and supplying prefiltered whole blood to a membrane filter having at least 5% of its pore volume constituted by pores having a pore cross section diameter larger than 10 microns.

There is also provided in accordance with a preferred embodiment of the invention a leukocyte filtering method comprising: supplying whole blood to a prefilter; and supplying prefiltered whole blood to a membrane filter downstream of the prefilter, said membrane filter being characterized in that no more than 30% of its pore volume is constituted by pores having a pore cross section diameter less than 3 microns.

There is also provided in accordance with a preferred embodiment of the invention leukocyte filtered whole blood characterized in that: it includes (i) less than one million leukocytes per unit of blood, and (ii) at least one of: (a) at least sixty percent of the number of platelets in non-filtered whole blood; and (b) at least ninety percent of the number of red cells in non-filtered whole blood. In accordance with a preferred embodiment of the invention, the leukocyte filtered whole blood is characterized in that it includes: at least sixty percent of the number of platelets in non-filtered whole blood; and at least ninety percent of the number of red cells in non-filtered whole blood. In accordance with a preferred embodiment of the invention, the leukocyte filtered whole blood is produced by a method including: supplying whole blood to a prefilter which captures less than 60% of incoming leukocytes; and supplying prefiltered whole blood to a non-cellulosic and generally homogenous membrane filter. In accordance with a preferred embodiment of the invention, the membrane filter is characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membranes filter is characterized in that at least 5% of the pore volume is constituted by pores having a pore cross section diameter larger than 10 microns. In accordance with a preferred embodiment of the invention, the membrane filter is characterized in that no more than 30% of the pore volume being constituted by pores having a pore cross section diameter less than 3 microns. In accordance with a preferred embodiment of the invention, the leukocyte filtered whole blood is produced by a method comprising: supplying whole blood to a prefilter; and supplying prefiltered whole blood to a membrane filter downstream of the prefilter, said membrane filter being characterized in that it has a pore surface area/membrane volume ratio larger than 6 square meters per milliliter of membrane volume. In accordance with a preferred embodiment of the invention, the leukocyte filtered whole blood is produced by a method comprising: supplying whole blood to a prefilter; and supplying prefiltered whole blood to a membrane filter downstream of the prefilter, said membrane filter being characterized in that it has a pore surface area/membrane mass ratio larger than 12 square meters per gram of membrane. In accordance with a preferred embodiment of the invention, the leukocyte filtered whole blood is produced by a method comprising: supplying whole blood to a prefilter; and supplying prefiltered whole blood to a membrane filter downstream of the prefilter, said membrane filter being characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, the leukocyte filtered whole blood is produced by a method comprising: supplying whole blood to a prefilter; and supplying prefiltered whole blood to a membrane filter downstream of the prefilter, said membrane filter being characterized in that at least 40% of its pore volume is constituted by pores having a pore cross section diameter of between 3 and 10 microns. In accordance with a preferred embodiment of the invention, the leukocyte filtered whole blood is produced by a method comprising; supplying whole blood to a prefilter; and supplying prefiltered whole blood to a membrane filter having at least 5% of its pore volume constituted by pores having a pore cross section diameter larger than 10 microns. In accordance with a preferred embodiment of the invention, the leukocyte filtered blood product is produced by a method comprising: supplying whole blood to a prefilter; and supplying prefiltered whole blood to a membrane filter downstream of the prefilter; said membrane filter being characterized in that no more than 30% of its pore volume is constituted by pores having a pore cross section diameter less than 3 microns.

There is also provided in accordance with a preferred embodiment of the invention leukocyte filtered whole blood produced by a method including: supplying whole blood to a prefilter which captures less than 60% of incoming leukocytes; and supplying prefiltered whole blood to a non-cellulosic and generally homogeneous membrane filter. In accordance with a preferred embodiment of the invention, the membrane filter is characterized in that it has a pore surface area/membrane volume ratio larger than 6 square meters per milliliter of membrane volume. In accordance with a preferred embodiment of the invention, the membrane filter is characterized in that it has a pore surface area/membrane mass ratio larger than 12 square meters per gram of membrane. In accordance with a preferred embodiment of the invention, the membrane filter comprises at least one layer of a generally homogeneous non-cellulosic membrane, wherein the total pore volume of pores having a diameter between 1–30 microns is less than 90% of the total pore volume. In accordance with a preferred embodiment of the invention, the membrane filter is characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns. In accordance with a preferred embodiment of the invention, no more than 60% of the pore volume is constituted by pores having a pore cross section diameter larger than 10 microns. In accordance with a preferred embodiment of the invention, the membrane filter is characterized in that at least 40% of its pore volume is constituted by pores having a pore cross section diameter of between 3 and 10 microns. In accordance with a preferred embodiment of the invention, the membrane filter is characterized in that at least 5% of the pore volume is constituted by pores having a pore cross section diameter larger than 10 microns. In accordance with a preferred embodiment of the invention, the membrane filter is characterized in that no more than 30% of the pore volume is constituted by pores having a pore cross section diameter less than 3 microns.

There is also provided in accordance with a preferred embodiment of the invention leukocyte filtered whole blood produced by a method comprising: supplying whole blood to a prefilter; and supplying prefiltered whole blood to a membrane filter downstream of the prefilter, said membrane filter being characterized in that it has a pore surface area/membrane volume ratio larger than 6 square meters per milliliter of membrane volume.

There is also provided in accordance with a preferred embodiment of the invention leukocyte filtered whole blood produced by a method comprising: supplying whole blood to be filtered of leukocytes to a prefilter; and supplying prefiltered whole blood to a membrane filter downstream of the prefilter, said membrane filter being characterized in that it has a pore surface area/membrane mass ratio larger than 12 square meters per gram of membrane.

There is also provided in accordance with a preferred embodiment of the invention leukocyte filtered whole blood produced by a method comprising: supplying whole blood to be filtered of leukocytes to a prefilter; and supplying prefiltered whole blood to a membrane filter downstream of the prefilter, said membrane filter being characterized in that it has a pore size distribution having a median pore size between 3 and 12 microns and having at least 40% of the pore volume being constituted by pores having a pore cross section diameter of between 3 and 10 microns and having at least 5% of the pore volume being constituted by pores having a pore cross section diameter larger than 10 microns.

There is also provided in accordance with a preferred embodiment of the invention leukocyte filtered whole blood produced by a method comprising: supplying whole blood to a prefilter; and supplying prefiltered whole blood to a membrane filter downstream of the prefilter, said membrane filter being characterized in that at least 40% of its pore volume is constituted by pores having a pore cross section diameter of between 3 and 10 microns.

There is also provided in accordance with a preferred embodiment of the invention leukocyte filtered whole blood product produced by a method comprising: supplying whole blood to a prefilter; and supplying prefiltered whole blood to a membrane filter having at least 5% of its pore volume constituted by pores having a pore cross section diameter larger than 10 microns.

There is also provided in accordance with a preferred embodiment of the invention leukocyte filtered whole blood produced by a method comprising: supplying whole blood to a prefilter; and supplying prefiltered whole blood to a membrane filter downstream of the prefilter, said membrane filter being characterized in that no more than 30% of its pore volume is constituted by pores having a pore cross section diameter less than 3 microns.

In the context of the present application, the following definitions are used throughout:

"Pore size" is pore diameter in microns or other units of length, calculated as a function of mercury intrusion pressure, assuming cylindrical pores and the appropriate value of mercury surface tension and contact angle.

"Median pore size" is that pore size, above and below which the same volume of mercury is pressed into the membrane, e.g. if the median pore size is 10 microns, then the total amount mercury in all pores of a size less than 10 microns is the same as the total amount of mercury in all pores of a size greater than 10 microns.

"Pore size distribution" is the population frequency distribution of pores whose size is determined as described above.

"Cumulative pore volume" is the total mercury volume pressed into pores of a given size range.

"Symmetric membrane" and "homogeneous membrane" are used synonymously to refer to a membrane wherein most pores of the membrane maintain approximately the same pore cross sectional diameter along the entire length of the pore through the thickness of the membrane structure, irrespective of the pore size distribution in the membrane.

"Pore cross section diameter" (or "pore diameter") is the diameter of the pore (assumed to be cylindrical) calculated as described above. "Pore size" and "pore diameter" are used synonymously throughout the present description and claims.

The present invention also seeks to provide a novel membrane leukoreduction filter, a filtering method and filtering blood products. The present inventors have found that contrary to teachings of the prior art, certain commercial membranes can be used to make efficient leukoreduction filters. Also, simpler structures than previously conceived were found to make for highly efficient filters. These novel structures comprise only two groups of layers, wherein individual layers within each group are generally identical (and need not have gradually or step-wise diminishing pore sizes or be arranged to have gradually or step-wise diminishing pore sizes). The first group acts as preliminary filter (prefilter), capturing gel particles, microaggregates and a certain fraction of the leukocytes. The second group of identical layers captures the remaining fraction of leukocytes.

The preliminary filter layer is typically made of non-woven sheets with relatively large diameter fibers (3.5–10 microns in diameter), although woven sheets and membranes not necessarily of the same structure as the filter membranes may also be employed for this purpose. The second layer is typically made of identical membrane sheets having a median pore size of 3–12 microns. In contrast to the teachings of the prior art, it was found that the membranes do not need to have an especially narrow pore size distribution (such as the total volume of pores of 2–30 micron size constituting more than 94% of the total pore volume). It was also found, in contrast to the teaching of the prior art that when used in accordance with the present invention, the non-woven sheets can be made of relatively large diameter fibers (3.5–10 microns vs. 1–3 microns as taught in the prior art). The filters of the present invention can be used without any post-treatment to filter packed red cell units or whole blood. If it is desired to recover platelets from either whole blood or platelet concentrates, the membrane and prefilter can be chemically treated to provide media combining efficient white cell retention and good platelet and red cell recovery (e.g. by the method described in U.S. Pat. No. 5,783,094, the disclosure of which is incorporated herein by reference).

In a preferred embodiment of the present invention, the filter is constructed of two groups of layers, each group containing generally identical layers of filter media. One group comprises non-cellulosic membranes, while the other group comprises the prefilter material, preferably non-woven sheets.

The group of membranes can be made of any biocompatible non-cellulosic polymer composition. For example nylon, polyvinyl chloride (PVC), PVC copoylmers, polyvinylidene fluoride sulfone polymers, polyester, polyketones, aromatic polyamides, polyimides, polycarbonate, polyphenylene oxide, polyvinyl acetate and the like can be used to form the membranes of the present invention. The membranes can be manufactured by processes known in the art, including but not limited to solution phase separation, thermal inversion, foaming and sintering. Preferably, the thickness of each membrane is less than 0.25 mm, preferably of thickness between about 0.05 mm and about 0.2 mm. As analyzed by mercury porosimetry, the membrane filter preferably has a median pore size of 3.0–12 $\mu$m.

In contrast to the teachings of the prior art, pore size distribution does not need to be especially narrow. Typically, pores in the range of 2–30 $\mu$m preferably constitute less than 94% of the total pore volume of the membrane. Also, in contrast to the teachings of the prior art, in a preferred embodiment of the invention, the membrane is essentially symmetrical and isotropic, having homogeneous pores throughout its bulk.

When a group of non-woven sheets is used in a prefilter or as a prefilter for the membrane, the group of sheets preferably has a mean fiber diameter larger than that necessary in filters of the prior art in which leukocytes are captured mostly by the non-woven material. The most preferred mean fiber diameter is 3.5–10 $\mu$m. The non-woven sheets can be made of various biocompatible materials, e.g., polyester, nylon, polypropylene, cellulose derivatives and the like. It will be understood, however, that other materials can be used in the construction of the prefilter portion, such as woven sheets or membranes having a pore structure and/or pore size distribution not necessarily the same as the pore structure or pore size distribution of the membranes used to construct the filter portion of the leukocyte filter.

Prior art methods for filtering blood, particularly whole blood, employ a prefilter, generally to prevent clogging of the filter membranes. The prefilters of the prior art may themselves be layers of membranes, or they may be woven or non-woven sheets. However, contrary to the teachings of the prior art, in accordance with the present invention the thickness of the prefilter, whether a group of non-woven sheets or other material, will typically be more than 0.5 mm. Also, in contrast to the prior art, in the present invention the group of preliminary filter layers (whether fabricated from non-woven sheets or from other materials, such as membranes different from the membranes or group of membranes used in the filter portion) can be made to capture less than 60% of all leukocytes, and the leukocyte filter will still be highly efficient in both leukocyte retention and volume recovery.

In constructing a leukocyte filter according to one preferred embodiment of the present invention, at least two membrane layers are stacked with at least two non-woven sheets and placed in an appropriate housing made of biocompatible plastic. Whole blood or blood fractions are allowed to flow through the filter by gravity. According to another preferred embodiment of the present invention a single membrane layer is stacked with at least two layers of non-woven sheets to make a leukocyte filter.

The membrane and non-woven fabric layers can be either untreated or treated. When untreated, whole blood and packed red cells can be efficiently leukoreduced. Platelets in whole blood are also retained by a filter so constructed. If it is desired to recover platelets from either whole blood or platelet-containing blood fractions, the filter media (both membrane and non-woven) need to be chemically treated to prevent blockage of the platelets. Such treatments can be, although need not necessarily be, in accordance with that described in U.S. Pat. No. 5,783,094, assigned to the present applicant/assignee, the disclosure of which is incorporated herein by reference. Such treatment efficiently coats all external and internal surfaces of the filter media and renders them platelet compatible. Physical and mechanical properties of the media are not affected by the treatment.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
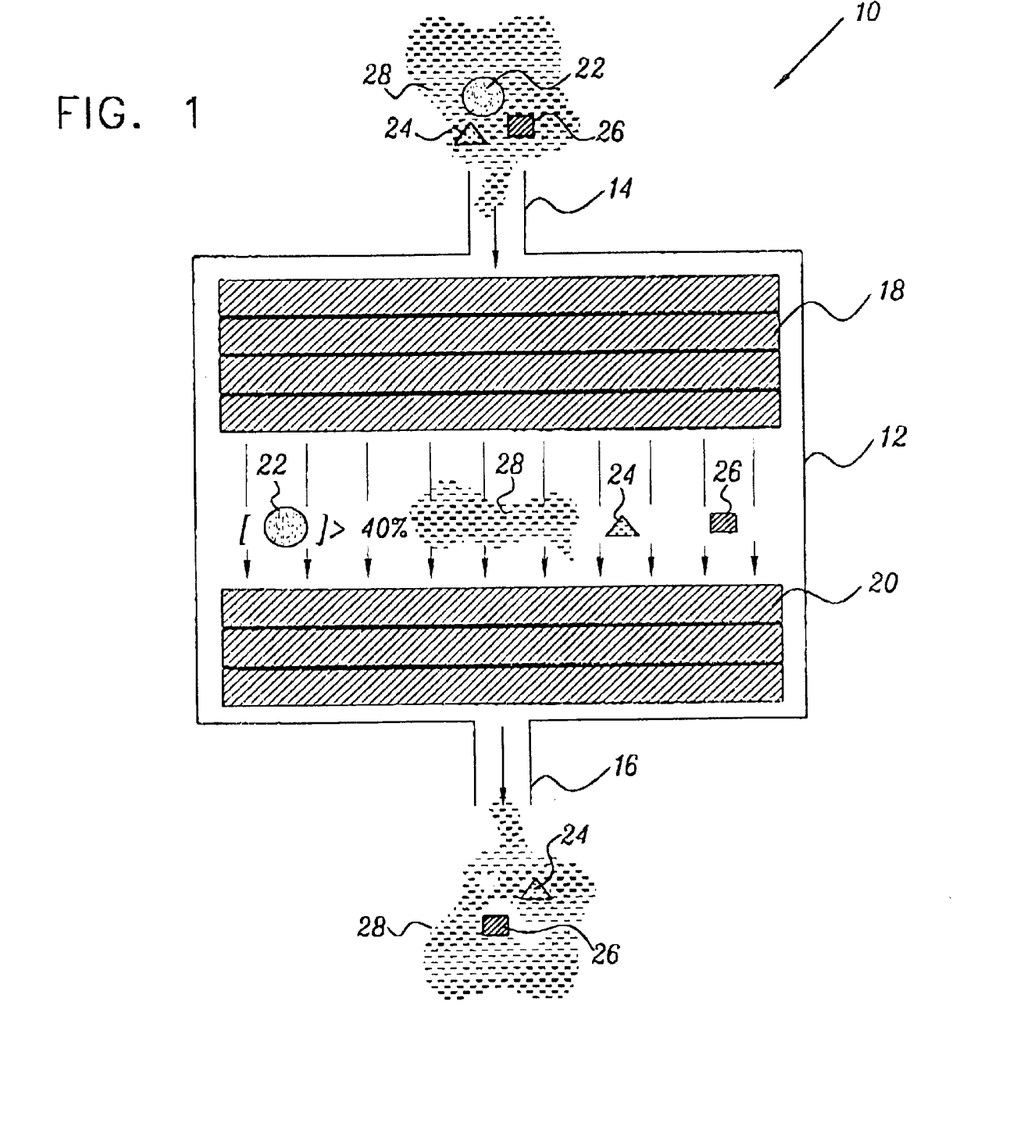
FIG. 1 is a simplified concept-level illustration of a leukocyte filter constructed and operative in accordance with a preferred embodiment of the invention.

Reference is now made to FIG. 1, which is a simplified concept-level illustration of a leukocyte filter constructed and operative in accordance with a preferred embodiment of the invention. As seen in FIG. 1 there is provided a whole blood leukocyte filter 10 typically comprising a filter housing 12 defining a whole blood inlet 14 and a leukocyte-filtered blood outlet 16.

Disposed in filter housing 12 is a prefilter portion 18 and downstream thereof a membrane filter portion 20. In accordance with a preferred embodiment of the present invention, the prefilter portion is characterized in that it captures less than 60% of incoming leukocytes, which are designated by reference numeral 22. The membrane filter portion 20 is preferably characterized in that it is non-cellulosic and generally homogeneous. Other whole blood components include red blood cells, which are designated by reference numeral 24, platelets, which are designated by reference numeral 26 and plasma, which are designated by reference numeral 28.

Figure 2:
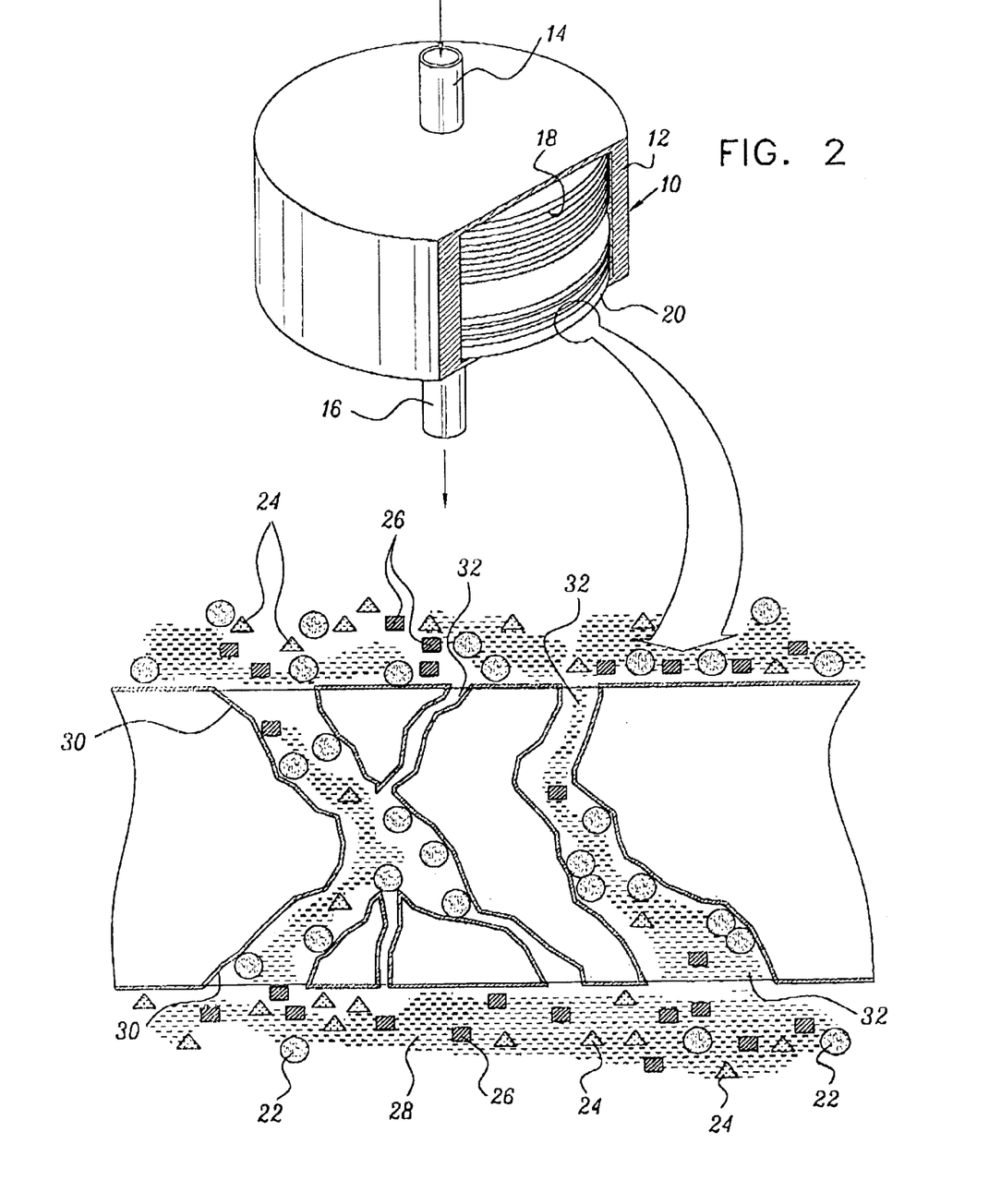
FIG. 2 is a simplified partially cut-away pictorial illustration of a leukocyte filter of the type shown in FIG. 1, illustrating a preferred membrane structure useful therein.

Reference is now made to FIG. 2, which is a simplified partially cut-away pictorial illustration of a leukocyte filter of the type shown in FIG. 1, illustrating a preferred membrane structure useful therein. For the sake of conciseness, the reference numerals employed in FIG. 1 are also employed in FIG. 2 for equivalent elements thereof.

As seen in FIG. 2, the membrane filter portion 20, downstream of the prefilter portion 18, is preferably characterized in that it has a pore surface area/membrane volume ratio larger than 6 square meters per milliliter of membrane volume. The pore surface area, as seen in section in FIG. 2, is constituted by the interior surfaces 30 of the various pores 32. The leukocytes 22 tend to adhere to interior surfaces 30 and are thus filtered out from the prefiltered whole blood supplied thereto. Preferably, the membrane filter portion is characterized in that it has a pore surface area/membrane weight ratio larger than 12 square meters per gram of membrane.

Figure 3A:
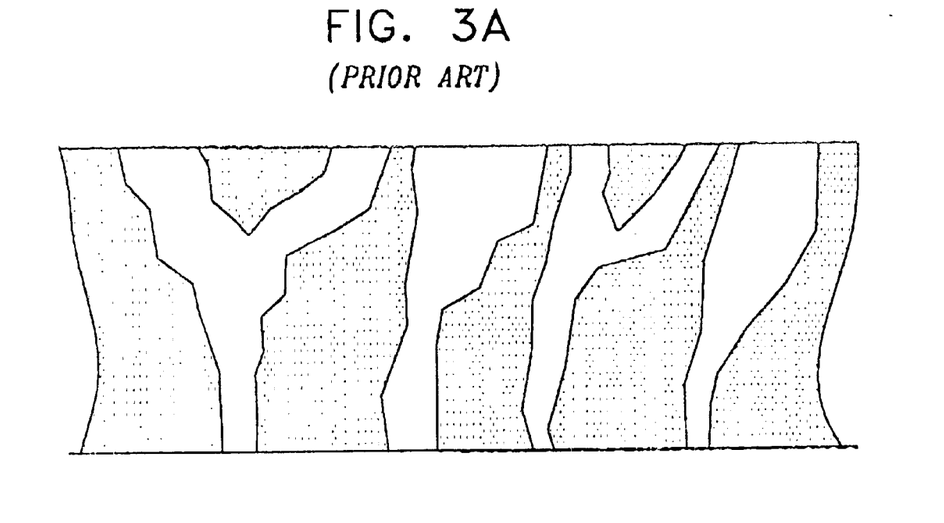
FIGS. 3A and 3B are simplified pictorial illustrations of respectively a prior art membrane structure and a homogeneous membrane structure useful in the filter of FIGS. 1 & 2 in accordance with a preferred embodiment of the present invention.
Figure 3B:
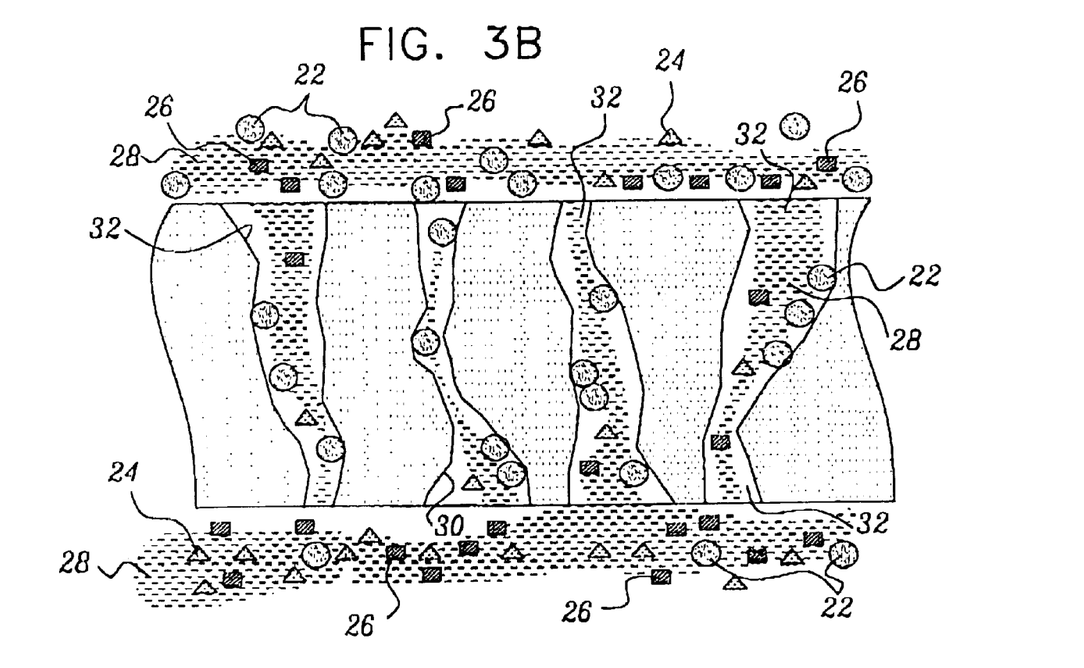

Reference is now made to FIGS. 3A & 3B which taken together illustrate another preferred feature of the present invention. Conventional leukocyte filters employ non-homogeneous membranes of the type shown in FIG. 3A. The non-homogeneous membranes are generally characterized in that they have larger pore cross sections at the upstream region of the membrane than at the downstream region thereof. The use of non-homogeneous membranes involves significant costs.

It is a preferred feature of the present invention that the membrane filter portion 20 thereof preferably employs homogeneous membranes, i.e. membranes which overall have upstream pore cross sections of generally the same size as downstream pore cross sections. This provides significant cost saving with substantially no degradation in filter quality. An example of such membranes is shown in FIG. 3B. As seen in FIG. 3B, in contrast to the membrane structure in FIG. 3A, the cross sections of the pores 32 may be larger or generally the same at the downstream region of the membrane as compared with the cross sections of the pores at the upstream region thereof.

Figure 4:
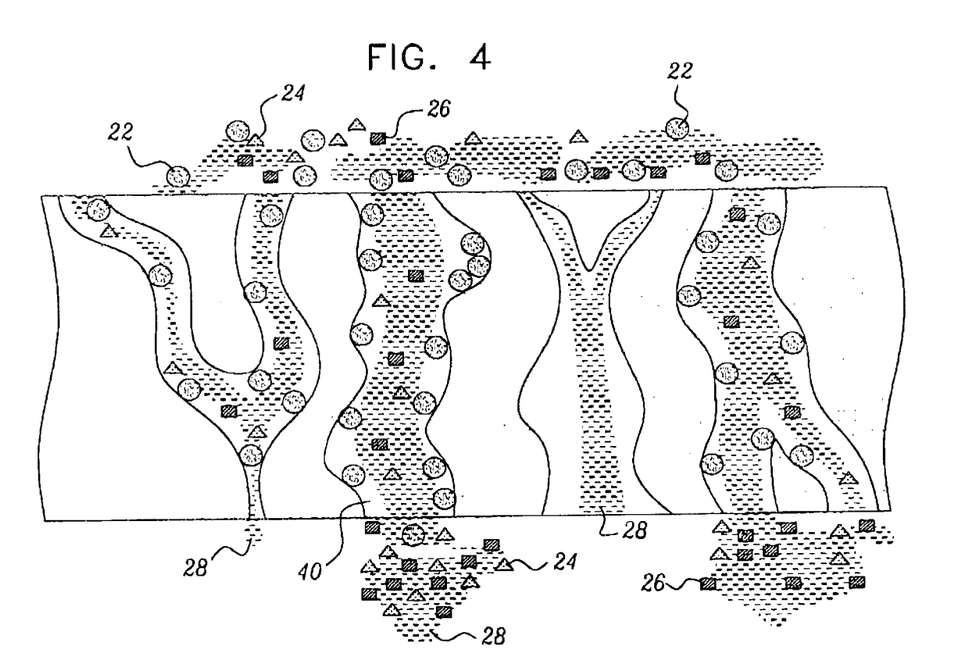
FIG. 4 is a simplified pictorial illustration of a preferred membrane structure useful in the filter of FIGS. 1 & 2 in accordance with a preferred embodiment of the present invention.

Reference is now made to FIG. 4, which is a simplified pictorial illustration of a preferred membrane structure useful in the filter of FIGS. 1 & 2 in accordance with a preferred embodiment of the present invention. As seen in FIG. 4, a membrane filter portion 20, downstream of the prefilter portion 18 is formed with at least some membrane layers having pores that are "leaky". By "leaky" is meant that the pore cross section is such that normally some leukocytes 22 flow therethrough. Thus, application of an excessive load of leukocytes on any individual membrane layer is avoided, thus reducing the likelihood of clogging. By using a group of membranes, good overall leukocyte filtering is nevertheless be achieved. While, as shown in FIG. 4, it is not necessarily true that all pores in a membrane are leaky, it is preferably true of some pores, such as the pore designated by reference numeral 40.

In accordance with a preferred embodiment of the present invention, the membrane filter portion has a pore size distribution having a median pore size between 3 and 12 microns and having at least 40% of the pore volume being constituted by pores having a pore cross section diameter of between 3 and 10 microns. Preferably at least 5% of the pore volume is constituted by pores having a pore cross section diameter larger than 10 microns.

Preferably, not more than 60% of the pore volume is constituted by pores having a pore cross section diameter larger than 10 microns.

In accordance with a preferred embodiment of the present invention, the membrane filter portion includes at least one layer of a generally homogeneous non-cellulosic membrane, wherein the total pore volume of pores in the membrane having a diameter between 1–30 microns is less than 90% of the total pore volume.

In accordance with a preferred embodiment of the present invention, the membrane filter portion is characterized in that no more than 30% of the pore volume is constituted by pores having a pore cross section diameter less than 3 microns.

Figure 5:
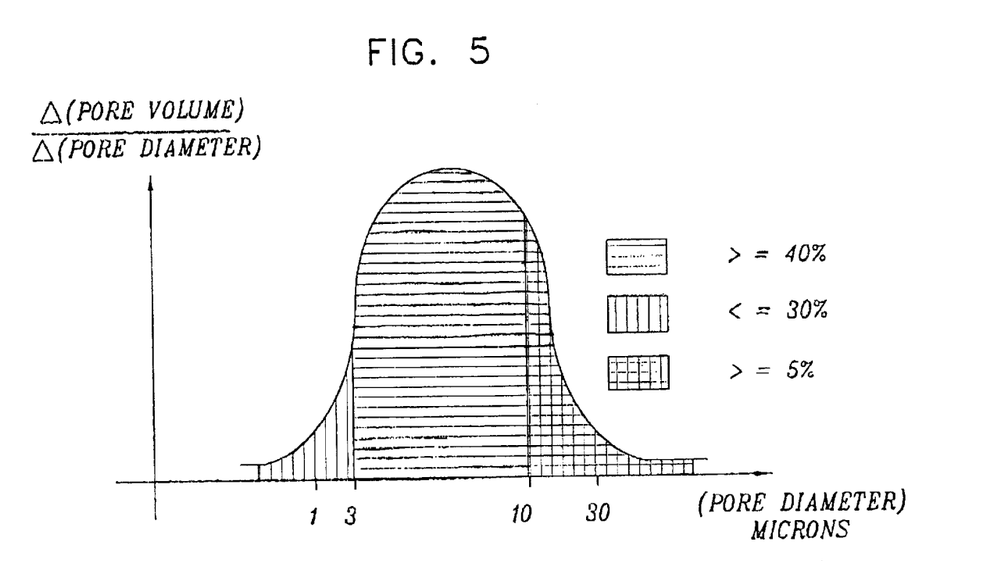
FIG. 5 is a simplified illustration of a preferred pore size distribution of a preferred membrane structure useful in the filter of FIGS. 1 & 2 in accordance with a preferred embodiment of the present invention.

A preferred pore size distribution is illustrated in FIG. 5, which shows a pore distribution wherein at least 40% of the cumulative (total) volume of all pores is located in pores of 3–10 micron diameter, less than 30% of the cumulative volume of all pores is located in pores less than 3 micron diameter, and at least 5% of the cumulative volume of all pores is located in pores of at least 10 micron diameter.

In accordance with one preferred embodiment of the present invention, a leukoreduction filter preferably includes at least one layer of a non-cellulosic membrane with a median pore size of 3.0–12 $\mu$m, as determined by mercury porosimetry. The membrane is preferably symmetric, i.e., there is preferably little difference in the size of each pore across the membrane thickness, irrespective of pore size distribution in the membrane. Each membrane layer preferably has a thickness of less than about 0.25 mm, preferably between about 0.05 mm and about 0.2 mm.

Preferably, membranes employed in the present invention are "tortuous path membranes", as contrasted to "track etched membranes". Track etched membranes have generally cylindrical pores going straight through the thickness of the membrane. Track etched membranes, used in some prior art, often have very poor throughput.

An example of a commercially available membrane suitable for the present invention is "VERSAPOR", a membrane made of a PVC-acrylonitrile (PVC-AN) copolymer and manufactured by Pall-Gelman, New York. Another example is "NYLON MAGNA", made by MSI-Osmonics, Massachusetts. The most preferred "Versapor" membrane has a median pore size of 5–5.5 microns, and the most preferred "Magna" membrane has a median pore size of 4.5–5.5 microns. Surprisingly, the present inventors have found that these commercially available membranes, in combination with an appropriately chosen preliminary filter, satisfactorily filter leukocytes from blood. Nylon and PVC-acrylonitrile copolymer are very different chemically. Since both types of membranes perform satisfactorily, it can be stated that chemical constitution is far less important in the context of the present invention than pore structure and pore distribution. This is especially true when the membranes are chemically post-treated, rendering their surface chemical properties independent of the chemistry of the base polymer.

A preferred median membrane pore size is 3–12 microns. A still more preferred median pore size is 5–9 microns. It was also found that a preferred pore size distribution is one wherein the pores between 2–10 microns constitute 70–90% of the total pore volume of the membrane.

Preferably, the number of membrane layers in the filter ranges from 1 to 10.

Preferably stacked together with (but not bonded to) the layers of the membrane are at least two layers of a preliminary filter material, preferably (but not necessarily) melt blown non-woven sheets with a mean fiber size of 3.5–10 $\mu$m. The layers of the preliminary filter material serve as a prefilter for the layers of the membrane. When this material comprises non-woven sheets, the non-woven material may be made of various biocompatible materials, e.g., polyester, nylon, polypropylene, cellulose derivatives and the like. Woven sheets and membranes not necessarily of the same structure as the membranes used as filter material may also be used as the preliminary filter material. Preferably, the number of preliminary filter layers ranges from 2 to about 30. The membrane layers and the preliminary filter material together form a filter stack, which is preferably disposed in a housing having a blood inlet and an outlet.

Thus, whereas in the prior art membranes with high asymmetry or an especially narrow pore size distribution are employed, membranes of the present invention are non-cellulosic preferably symmetric membranes with a median pore size of 3–12 microns. Also, whereas in the prior art membranes with limited leukocyte capacity are used, requiring a preliminary filter capturing a majority of the leukocytes, membranes of the present invention enable the use of preliminary filters with lower capacity.

The above described embodiment not only filters out leukocytes, it also generally blocks passage of platelets. In accordance with another preferred embodiment of the present invention, the layers of the membrane and non-woven material are treated by a post-treatment, such as that described in U.S. Pat. No. 5,783,094, which treatment imparts hydroxylic functionality to the surfaces of the membrane and the non-woven material. The layers thus treated pass, instead of block, platelets. In such an embodiment, the leukocyte filter can be used to recover platelets from whole blood or a platelet-containing blood fraction.

Several illustrative examples of the present invention are now described.

EXAMPLE 1

Whole Blood Filter with Platelet Recovery—Nylon

Nylon membrane sheets (MAGNA, Osmonics), which constitute an example of the type of membrane shown in FIG. 3B or FIG. 4, were surface coated by dipping into an aqueous hydroxypropyl cellulose solution as per U.S. Pat. No. 5,783,094. The membrane was then dried in an oven at 80° C. for 1 hr. Non-woven polyester sheets (120 g/m$^2$, median fiber size 4 $\mu$m) were treated likewise.

The treated membrane and non-woven sheets were cut into squares of 10×10 cm. Four layers of membrane were stacked onto (but not bonded to) 20 layers of non-woven sheets and placed in a housing with a blood inlet and an outlet, whereby to form a filter of the type shown in FIG. 1.

A unit of anticoagulated whole human blood was connected to the housing inlet and was filtered at a head of 60 cm, i.e. the blood was placed 60 cm above the filter. Filtration was complete in about 25 min.

Analysis of the filtrate showed a red cell recovery of 92%, a platelet recovery of 77% and a residual white cell count of 0.6 million.

EXAMPLE 2

Pore Size Distribution of Nylon Membrane

The membrane of example 1 was subjected to mercury porosimetry. This analysis showed a median pore size of 5.2 micrometer. Total pore volume of pores of pore size between 1–30 micrometers was 89%. Total pore volume of pores of pore size between 3–10 micrometers was 81%. Total pore volume of pores of pore size larger than 10 micrometers was 7%. Total pore volume of pores of pore size smaller than 3 micrometers was 12%. The specific surface area of the membrane was 25.8 m$^2$/g. The pore volume/pore size distribution falls within the distribution shown in FIG. 5.

EXAMPLE 3

Whole Blood Filter with Platelet Recovery

A PVC-AN membrane (VERSAPOR, Pall-Gelman), which constitutes an example of the type of membrane shown in FIG. 3B or FIG. 4, was surface-treated as described in Example 1. Non-woven polyester was treated likewise. The membrane and non-woven materials were cut into circle of 3.5 cm in diameter. Five membrane circles were stacked onto 18 non-woven circles and placed in a housing, whereby to form a filter of the type shown in FIG. 1. Sixty ml of whole blood were passed through the filter by gravity. Analysis of the filtrate showed a platelet recovery of 76% and residual white cell count of 0.19 million.

EXAMPLE 4

Pore Size Distribution of PVC-AN Membrane

The membrane of Example 3 was analyzed by mercury porosimetry. The analysis showed a median pore size of 5.3 micron. Total pore volume of pores between 3–10 microns was 79%. Total pore volume of pores larger than 10 micrometers was 9%. Pore volume of pores smaller than 3 micrometers was 12%. The specific surface area of the membrane was 14.1 $m^2/g$. The pore volume/pore size distribution falls within the distribution shown in FIG. 5.

EXAMPLE 5 (Comparative)

Whole Blood Filter with Platelet Recovery—PVC-AN

The experiment was run in a mode similar to Example 3, except that the membrane layers were interspersed among the non-woven layers. Platelet recovery was 66% and residual white cell count was 0.08 million.

EXAMPLE 6

Whole Blood Filter without Platelet Recovery—Nylon

Nylon membranes constituting an example of the type of membranes shown in FIG. 5B or FIG. 4, and non-woven polyester sheets were used as in Example 1, except that they were not surface treated. Filter size was as in Example 3. Sixty-three ml of whole blood were passed through the filter. Analysis of the filtrate showed a red cell recovery of 76%, same as the volume recovery, platelet passage of 4% and residual white cell count of 0.04 million.

EXAMPLE 7

Platelet Concentrate Filter

Nylon membranes constituting an example of the type of membranes shown in FIG. 3B or FIG. 4, and polyester non-woven sheets were surface treated as described in Example 1. Four membrane layers were put on top of 18 layers of non-woven material, and the stack was sealed in a housing, whereby to form a filter of the type shown in FIG. 1. Fifty-five ml of platelet concentrate were passed through the filter by gravity. Analysis of the filtrate showed a platelet recovery of 83% and a residual white cell count of 0.08 million.

EXAMPLE 8

Single Membrane Filter

A nylon membrane constituting an example of the type of membrane shown in FIG. 3B or FIG. 4 and non-woven sheets were treated as in Example 1. One layer of membrane and 24 layers of non-woven material were placed in a housing, whereby to form a filter of the type shown in FIG. 1. Whole blood was filtered through the assembled filter. The filtrate contained 87% of the original platelet concentration and only 0.3 million leukocytes.

EXAMPLE 9

Pore Size Distribution

The nylon membrane of Example 8 was subjected to pore size distribution analysis by mercury porosimetry. Total pore volume of pores of pore size between 1 and 30 micrometers was found to be 83%. Total pore volume of pores of pore size between 3–10 micrometers was found to be 59%. Total pore volume of pores of pore size larger than 10 micrometers was 13%. Total pore volume of pores of pore size smaller than 3 micrometers was 28%. The specific surface area of the membrane was 25.6 $m^2/g$. The pore volume/pore size distribution falls within the distribution shown in FIG. 5.

It will be appreciated by persons skilled in the art that the present invention is not limited by what has been particularly shown and described hereinabove. Rather the scope of the present invention include both combinations and subcombinations of the various features described hereinabove as well as variations and modifications which would occur to persons skilled in the art upon reading the specification and which are not in the prior art.

What is claimed is:

1. A leukocyte filter comprising:

a prefilter portion; and a multilayered membrane filter portion downstream of the prefilter portion, said membrane filter portion employing at least one generally homogeneous membrane and having a pore size distribution having a median pore size between 5 and 12 microns and having at least 40% of the pore volume being constituted by pores having a pore cross section diameter of between 3 and 10 microns and having at least 5% of the pore volume being constituted by pores having a pore cross section diameter larger than 10 microns, wherein the pore volume of pores having a diameter between 1–30 microns is less than 90% of the total pore volume.

2. A leukocyte filter according to claim 1 and wherein said membrane filter portion is characterized in that no more than 30% of the pore volume is constituted by pores having a pore cross section diameter less than 3 microns.

3. A leukocyte filter comprising:

a prefilter portion; and a multilayered membrane filter portion downstream of the prefilter portion, said membrane filter portion comprising at least one layer of a generally homogeneous non-cellulosic membrane, wherein the pore volume of pores having a diameter between 1–30 microns is less than 90% of the total pore volume and wherein said membrane filter portion has a median pore size of 5–12 microns, and wherein the pore volume of pores having a diameter exceeding 10 microns is at least 5% of the total pore volume.

4. A leukocyte filter according to claim 3 and wherein said membrane filter portion is characterized in that at least 40% of the pore volume is constituted by pores having a pore cross section diameter of between 3 and 10 microns.

* * * * *